United States Patent
Hamura et al.

(10) Patent No.: US 11,905,367 B2
(45) Date of Patent: Feb. 20, 2024

(54) BRANCHED MONODISPERSED POLYETHYLENE GLYCOL, INTERMEDIATE AND METHODS FOR PRODUCING SAME

(71) Applicant: NOF CORPORATION, Tokyo (JP)

(72) Inventors: Mika Hamura, Kawasaki (JP); Yuki Matsuno, Kawasaki (JP); Hiroki Yoshioka, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 311 days.

(21) Appl. No.: 16/981,395

(22) PCT Filed: Mar. 19, 2019

(86) PCT No.: PCT/JP2019/011594
§ 371 (c)(1),
(2) Date: Sep. 16, 2020

(87) PCT Pub. No.: WO2019/181984
PCT Pub. Date: Sep. 26, 2019

(65) Prior Publication Data
US 2021/0009757 A1    Jan. 14, 2021

(30) Foreign Application Priority Data

Mar. 20, 2018 (JP) ................ 2018-052365

(51) Int. Cl.
*C08G 65/331* (2006.01)
*C08G 65/333* (2006.01)

(52) U.S. Cl.
CPC ...... *C08G 65/3311* (2013.01); *C08G 65/3332* (2013.01)

(58) Field of Classification Search
None
See application file for complete search history.

(56) References Cited

U.S. PATENT DOCUMENTS

| | | | |
|---|---|---|---|
| 2004/0203081 A1 | 10/2004 | James et al. | |
| 2005/0058620 A1 | 3/2005 | Nakamoto et al. | |
| 2005/0288490 A1* | 12/2005 | Nakamoto | A61P 43/00 |
| | | | 530/385 |
| 2006/0073113 A1 | 4/2006 | Nakamoto et al. | |
| 2006/0074009 A1 | 4/2006 | James et al. | |
| 2006/0115450 A1 | 6/2006 | Nakamoto et al. | |
| 2006/0172933 A1 | 8/2006 | James et al. | |
| 2009/0192320 A1 | 7/2009 | Nakamoto et al. | |
| 2010/0216714 A1 | 8/2010 | James et al. | |
| 2011/0033527 A1 | 2/2011 | Wu et al. | |
| 2011/0040113 A1* | 2/2011 | Wu | C08G 65/329 |
| | | | 568/679 |
| 2011/0082277 A1 | 4/2011 | Nakamoto et al. | |
| 2012/0232169 A1 | 9/2012 | Wu et al. | |
| 2013/0052130 A1 | 2/2013 | Davis et al. | |
| 2018/0312633 A1* | 11/2018 | Ota | C07D 317/22 |
| 2018/0362712 A1 | 12/2018 | Zhu et al. | |

FOREIGN PATENT DOCUMENTS

| | | | |
|---|---|---|---|
| CN | 102665685 A | 9/2012 | |
| CN | 106905120 A | 6/2017 | |
| JP | 2004-197077 A | 7/2004 | |
| JP | 2008-500375 A | 1/2008 | |
| JP | 2009-102649 A | 5/2009 | |
| JP | 2012-528857 A | 11/2012 | |
| WO | 2010/141069 A2 | 12/2010 | |
| WO | 2017/057612 A1 | 4/2017 | |
| WO | WO-2017057612 A1 * | 4/2017 | ............ A61K 47/34 |
| WO | 2017/107823 A1 | 6/2017 | |

OTHER PUBLICATIONS

Communication dated Jul. 26, 2022 issued by the Japanese Intellectual Property Office in counterpart Japanese Application No. 2019-051107.
Communication dated Jun. 30, 2022 issued by the State Intellectual Property Office of P.R. China in counterpart Chinese application No. 201980020565.7.
Lyon et al., "Reducing hydrophobicity of homogeneous antibody-drug conjugates improves pharmacokinetics and therapeutic index," Nature Biotechnology, vol. 33, No. 7, pp. 733-735, Jul. 2015, doi:10.1038/nbt.3212, pp. 733-736 (Total 4 pages).
Schuster et al., "Effects of chemical structure on the dynamic and static surface tensions of short-chain, multi-arm nonionic fluorosurfactants," Journal of Colloid and Interface Science 428 (2014), pp. 276-285 (Total 10 pages).
International Search Report dated Jun. 4, 2019 (PCT/ISA/210) issued by the International Searching Authority for International Application No. PCT/JP2019/011594.
Written Opinion dated Jun. 4, 2019 (PCT/ISA/237) issued by the International Searching Authority for International Application No. PCT/JP2019/011594.

(Continued)

*Primary Examiner* — Christopher M Rodd
(74) *Attorney, Agent, or Firm* — Sughrue Mion, PLLC

(57) ABSTRACT

A branched monodispersed polyethylene glycol represented by the formula (1):

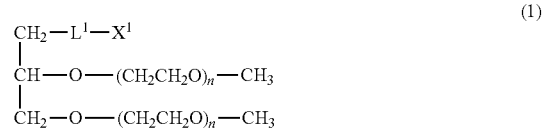

wherein $X^1$ is a functional group that forms a covalent bond upon a reaction with a functional group present in a biofunctional molecule; n is an integer of 4 to 50, which represents number of repeating units of ethylene oxide units; and $L^1$ represents a single bond, —NH—, $-L^2-(CH_2)_{m1}-$ or $-L^2-(CH_2)_{m1}-L^3-(CH_2)_{m2}-$, $L^2$ represents an ether bond, an amide bond, an urethane bond or a single bond, $L^3$ represents an ether bond, an amide bond or an urethane bond, and m1 and m2 represent each independently an integer of 1 to 5.

5 Claims, No Drawings

(56) References Cited

OTHER PUBLICATIONS

Communication dated Nov. 18, 2021, from the European Patent Office in European Application No. 19770451.3.
Schuster Thomas et al., Appendix A. Supplementary material—Effects of chemical structure on the dynamic and static surface tensions of short-chain, multi-arm nonionic fluorosurfactants, Journal of Colloid and Interface Science, Aug. 1, 2014 (Aug. 1, 2014), pp. 1-33, XP055859507.
Communication dated Oct. 11, 2022 by the Korean Intellectual Property Office in Korean Patent Application No. 10-2020-7027023.

* cited by examiner

BRANCHED MONODISPERSED POLYETHYLENE GLYCOL, INTERMEDIATE AND METHODS FOR PRODUCING SAME

CROSS-REFERENCE TO RELATED APPLICATIONS

This application is a National Phase Entry of PCT International Application No. PCT/JP2019/011594, filed on Mar. 19, 2019, which claims priority to Japanese Patent Application No. 2018-052365 filed on Mar. 20, 2018, the contents of all of which are incorporated herein by reference in their entirety.

TECHNICAL FIELD

The present invention relates to a highly pure branched monodispersed polyethylene glycol having a chemically reactive functional groups, an intermediate of the branched monodispersed polyethylene glycol, and methods for producing them. More particularly, it relates to a branched monodispersed polyethylene glycol, which is used for modification of a biofunctional molecule such as a physiologically active protein, a peptide, an antibody, a nucleic acid or a low-molecular weight drug, a drug carrier in a drug delivery system, a diagnostic material, a medical device or the like and which is particularly useful for modification of a drug in an antibody drug.

BACKGROUND ART

In the drug field, since many of the low-molecular weight drugs excellent in physiological effects are hydrophobic substances, there is a defect that it is difficult to utilize them in a living body owing to low solubility and aggregation thereof. Thus, there have been developed utilization of a solubilizing agent and a drug delivery technique using a drug carrier such as liposome or polymer micelle.

As one of delivery techniques of the low-molecule weight drug, an antibody-drug conjugate (Antibody-Drug Conjugate: ADC) may be exemplified, and ADC is an antibody drug in which a drug is bonded to an antibody and which aims to actively carry the drug to a disease site by utilizing the antigen specificity of the antibody. In recent years, it is one of the most rapidly growing techniques in the field of cancer treatment. ADC is composed of each part of an antibody, a drug and a linker for linking the antibody and the drug.

Many of the drugs used in ADC are hydrophobic and when a plurality of these hydrophilic drugs are bonded to an antibody to prepare ADC, there is a problem of occurrence of aggregation or decrease in stability of the antibody in blood, which are caused by the hydrophobicity of the drugs. Accordingly, the number of the drugs which can be mounted per antibody is restricted and as a result, the medicinal effect of ADC cannot be sufficiently obtained in some cases.

One of the solutions to be investigated for the problem is the use of a hydrophilic linker. As the hydrophilic linker, polyethylene glycol, a hydrophilic peptide, a sugar chain and the like are used. In particular, since polyethylene glycol has a low antigenicity and a high biocompatibility, it is used in a plurality of ADC in clinical trial and preclinical trial stages.

Moreover, in the field of ADC, for the purpose of guaranteeing the uniformity of ADC and simplifying purification, analysis and application for drug approval, a compound containing 90% or more of a component having a specific ethylene glycol chain length is used. Such a compound is referred to as a monodispersed polyethylene glycol.

In recent years, there has been reported ADC in which a monodispersed polyethylene glycol is not used as a linker main chain that links an antibody and a drug but a monodispersed polyethylene glycol is introduced as a side chain into a linker that links an antibody and a drug.

In Non Patent Literature 1, the pharmacokinetics and therapeutic effect are compared between ADC in which monodispersed polyethylene glycol is used as a linker main chain that links an antibody and a drug and ADC in which monodispersed polyethylene glycol is used as a side chain of a linker that links an antibody and a drug, and it is reported that the latter ADC has a high effect of masking the hydrophobicity of the drug and exhibits excellent pharmacokinetics and therapeutic effect. In ADC in which a monodispersed polyethylene glycol is used as a linker main chain, since the drug is bonded to a terminal of the monodispersed polyethylene glycol, when a long linker is used, the hydrophobic drug is exposed to the outside of the antibody, the hydrophobicity of ADC increases, and the stability in blood decreases. In ADC in which a monodispersed polyethylene glycol is used as a side chain of the linker, the drug is adjacent to the antibody owing to the use of a short linker and the monodispersed polyethylene glycol chain of the side chain is arranged so as to cover the drug, so that it is presumed that the hydrophobicity of the drug is effectively masked.

As mentioned above, in the ADC field, how much degree of the hydrophobicity of the drug can be masked is important. In the literatures reported hitherto, it is common to suppress the generation of aggregation and the decrease in stability of the antibody in blood resulting from the hydrophobicity of the drug by using a hydrophilic linker. However, it becomes possible to effectively mask the hydrophobicity of the drug by directly bonding the monodispersed polyethylene glycol not to a linker but to the drug. In addition, it is considered that the hydrophobicity of the drug can be more effectively masked when the monodispersed polyethylene glycol to be bonded to the drug has a branched structure having a plurality of polyethylene glycol chains per one reaction point as compared with a structure having one polyethylene glycol chain per one reaction point.

Patent Literature 1 discloses a branched polyethylene glycol capable of effective modification with polyethylene glycol due to introduction of two polyethylene glycol chains per one reaction point, which has a functional group that forms a covalent bond upon a reaction with a functional group present in a biofunctional molecule on the primary carbon at the 1-position of a glycerin backbone and polyethylene glycol chains at the 2- and 3-positions. However, the branched polyethylene glycol described in Patent Literature 1 is a so-called polydispersed polymer in which the polyethylene glycol chains are bonded by a polymerization reaction, and the molecular weight is not monodispersed. At the production of ADC, since the number of the bonded drugs is usually confirmed using a mass spectrometer or HPLC, there is a problem in the production that the confirmation thereof becomes difficult when a compound having a different ethylene glycol chain length is present as an impurity in a linker material. In addition, since equivalents of the antibody and the drug to be added at the production of ADC become unclear when the compound having a different ethylene glycol chain length is present as an impurity, there arise a problem that it becomes necessary to excessively use expensive antibody and drug and a problem that compounds having a plurality of molecular weights are occurred at the application for drug and the identification of compounds and performance of various tests become complex.

Moreover, Patent Literature 2 discloses a branched monodispersed polyethylene glycol in which three or four monodispersed ethylene glycol chains are introduced by bonding monodispersed polyethylene glycols to a branched site composed of trishydroxymethylaminomethane or an amino acid such as lysine. As the method for purifying the branched monodispersed polyethylene glycol, for example, recrystallization and column purification are exemplified. In Patent Literature 2, the monodispersed polyethylene glycol added in excess at the time of the reaction is removed by column chromatography. However, the purification method by column chromatography has a problem that it is not suitable for industrial mass production because the operation is complicated and causes a decrease in yield.

Therefore, there are desired a highly pure branched monodispersed polyethylene glycol having a functional group that forms a covalent bond upon a reaction with a biofunctional molecule and a plurality of monodispersed polyethylene glycol chains, and a production method which is simple and suitable for mass production thereof.

CITATION LIST

Non Patent Literature

Non Patent Literature 1: Nature Biotechnology, 2015, 33, 733-735

Patent Literature

Patent Literature 1: JP-A-2004-197077
Patent Literature 2: US20130052130A1

SUMMARY OF INVENTION

Problem to be Solved by the Invention

An object of the present invention is to provide a highly pure branched monodispersed polyethylene glycol that effectively masks the hydrophobicity of a drug, an intermediate of the branched monodispersed polyethylene glycol, and production methods capable of easily obtaining the branched monodispersed polyethylene glycol and the intermediate.

Means for Solving the Problem

As a result of the intensive studies to solve the problem described above, the present inventors have found that, as shown in the formula (1), there is obtained a branched monodispersed polyethylene glycol which has a functional group that forms a covalent bond upon a reaction with a functional group present in a biofunctional molecule on the primary carbon at the 1-position of a glycerin backbone and monodispersed polyethylene glycol chains at the 2- and 3-positions. Furthermore, the inventors have found that, when an intermediate for producing the branched monodispersed polyethylene glycol is synthesized using a specific functional group at the terminal, the highly pure branched monodispersed polyethylene glycol can be obtained by only simple extraction without using a purification method by column chromatography, and thus have accomplished the present invention.

[1] A branched monodispersed polyethylene glycol represented by formula (1):

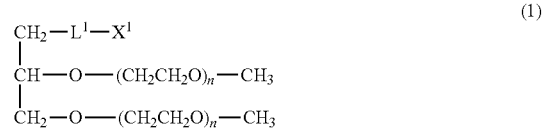

(1)

(in the formula (1), $X^1$ is a functional group that forms a covalent bond upon a reaction with a functional group present in a biofunctional molecule; n is an integer of 4 to 50, which represents number of repeating units of ethylene oxide units; and $L^1$ represents a single bond, —NH—, -$L^2$-$(CH_2)_{m1}$- or -$L^2$-$(CH_2)_{m1}$-$L^3$-$(CH_2)_{m2}$-, $L^2$ represents an ether bond, an amide bond, an urethane bond or a single bond, $L^3$ represents an ether bond, an amide bond or an urethane bond, and m1 and m2 represent each independently an integer of 1 to 5.)

[2] The branched monodispersed polyethylene glycol of [1], wherein $X^1$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

[3] An intermediate of a branched monodispersed polyethylene glycol, which is represented by formula (2):

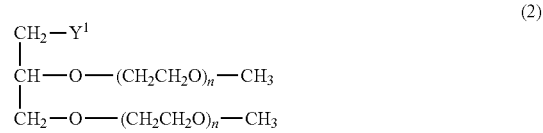

(2)

(in the formula (2), $Y^1$ is a hydroxyl group or an amino group; and n is an integer of 4 to 50, which represents number of repeating units of ethylene oxide units.)

[4] A method for producing the intermediate of [3], wherein the following three steps:
a step (A) of coupling a monodispersed polyethylene glycol derivative represented by following formula (3) and a compound represented by following formula (4) to obtain a compound represented by following formula (5):

$$A\text{-}(CH_2CH_2O)_n\text{—}CH_3 \qquad (3)$$

(in the formula (3), A is a leaving group; and n is an integer of 4 to 50, which represents number of repeating units of ethylene oxide units.);

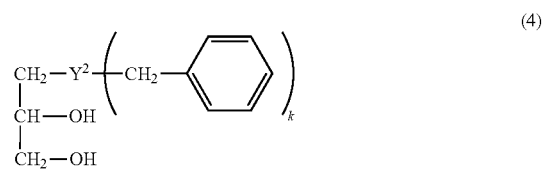

(4)

(in the formula (4), $Y^2$ is an oxygen atom or a nitrogen atom; and k is an integer of 1 or 2, and k is 1 when $Y^2$ is an oxygen atom, and k is 2 when $Y^2$ is a nitrogen atom.);

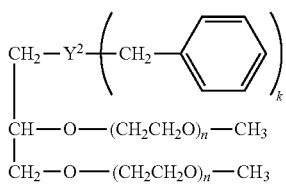

(5)

(in the formula (5), $Y^2$ is an oxygen atom or a nitrogen atom; n is an integer of 4 to 50, which represents number of repeating units of ethylene oxide units, k is an integer of 1 or 2, and k is 1 when $Y^2$ is an oxygen atom, and k is 2 when $Y^2$ is a nitrogen atom.);

a step (B) of subjecting the compound represented by the formula (5) to extraction purification with water and an organic solvent, and a step (C) of performing a treatment of cleaving the benzyl group contained in the compound represented by the formula (5) to obtain the intermediate of the branched monodispersed polyethylene glycol represented by the formula (2), are performed in the order of the step (A), the step (B) and the step (C).

[5] The method of [4], wherein the step (C) is effected by performing a catalytic hydrogen reduction treatment.

[6] A method for producing the branched monodispersed polyethylene glycol of [1], comprising a step (D) of converting $Y^1$ of the intermediate of [3] into $L^1$-$X^1$.

Effect of the Invention

According to the present invention, there can be provided a highly purified branched monodispersed polyethylene glycol that effectively masks the hydrophobicity of a drug, an intermediate of the branched monodispersed polyethylene glycol, and production methods capable of conveniently obtaining the branched monodispersed polyethylene glycol and the intermediate.

EMBODIMENTS FOR CARRYING OUT THE INVENTION

The present invention will be described in detail below.

The branched monodispersed polyethylene glycol in the invention is a compound which has a reactive functional group on the primary carbon at the 1-possition of a glycerin backbone and in which a monodispersed polyethylene glycol chain whose terminal is capped with a methoxy group is bonded to the 2- and 3-positions. A monodispersed polyethylene glycol referrers to a compound in which the purity of a component having a specific ethylene glycol chain length (hereinafter referred to as chain length purity) is 90% or more.

The branched monodispersed polyethylene glycol is represented by the formula (1).

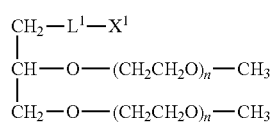

(1)

$X^1$ in the formula (1) is not particularly limited as far as it is an atomic group containing at least a functional group that forms a covalent bond upon a reaction with a functional group present in a biofunctional molecule (for example, a physiologically active protein, a peptide, an antibody, a nucleic acid or a low-molecular weight drug), which is a target for modification with the branched monodispersed polyethylene glycol. Examples of the functional group include functional groups described, for example, in "Hermanson, G. T. Bioconjugate Techniques, 2nd ed.; Academic Press: San Diego, CA, 2008", "Harris, J. M. Poly(Ethylene Glycol) Chemistry; Plenum Press: New York, 1992", and "PEGylated Protein Drugs: Basic Science and Clinical Applications; Veronese, F. M., Ed.; Birkhauser: Basel, Switzerland, 2009".

Among them, the functional group contained in $X^1$ in the formula (1) is preferably a functional group capable of reacting under mild conditions and with a high reaction efficiency with a functional group (for example, an amino group, a thiol group, an aldehyde group or a carboxyl group) present in a naturally occurring biofunctional molecule represented by a protein or a functional group (for example, a maleimide group, a ketone group, an azide group or an alkynyl group) capable of being artificially introduced into the biofunctional molecule described above. More specifically, it is preferably an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a 2-pyridyldithio group, an α-haloacetyl group, an alkynyl group, an allyl group, a vinyl group, an amino group, an oxyamino group, a hydrazide group, an azide group or a dibenzocyclooctyne (DBCO) group. Further, taking the reaction efficiency into consideration, it is preferably an active ester group, an active carbonate group, a maleimide group, an α-haloacetyl group, an alkynyl group, an azide group or a dibenzocyclooctyne (DBCO) group.

In still more specifically, the functional group contained in $X^1$ in the formula (1) is preferably an active ester group, an active carbonate group, an aldehyde group, an isocyanate group, an isothiocyanate group, an epoxy group, a maleimide group, a vinyl sulfone group, an acryl group, an α-haloacetyl group, a sulfonyloxy group or a carboxy group in the case where the functional group present in the biofunctional molecule as the target for modification is an amino group; preferably an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a 2-pyridyldithio group, an α-haloacetyl group, an alkynyl group, an allyl group or a vinyl group in the case where the functional group present in the biofunctional molecule as the target for modification is a thiol group; preferably a thiol group, an amino group, an oxyamino group or a hydrazide group in the case where the functional group present in the biofunctional molecule as the target for modification is an aldehyde group or a carboxy group; preferably a thiol group, an amino group, an oxyamino group, a hydrazide group or an azide group in the case where the functional group present in the biofunctional molecule as the target for modification is an alkynyl group; preferably an alkynyl group or a dibenzocyclooctyne group in the case where the functional group present in the biofunctional molecule as the target for modification is an azide group; and preferably a thiol group or an amino group in the case where the functional group present in the biofunctional molecule as the target for modification is a halogenated alkyl group, an alkylsulfonic acid ester or an arylsulfonic acid ester.

Here, the "active ester group" indicates an activated carboxy group represented by the formula: —C(=O)-D, wherein D represents a leaving group. The leaving group represented by D includes a succinimidyloxy group, a phthalimidyloxy group, a 4-nitrophenoxy group, a 1-imidazolyl group, a pentafluorophenoxy group, a benzotriazol-1-yloxy group, a 7-azabenzotriazol-1-yloxy group and the like. The "active carbonate" indicates an activated carbonate group represented by the formula: —O—C(=O)-D, wherein D represents a leaving group the same as that described above.

In a preferred embodiment of the invention, $X^1$ is a group represented by Group (I), Group (II), Group (III), Group (IV), Group (V) or Group (VI).

Group (I): A functional group capable of forming a covalent bond upon a reaction with an amino group of the biofunctional molecule The following (a), (b-1), (b-2), (c), (d), (e) and (f):

Group (II): A functional group capable of forming a covalent bond upon a reaction with a thiol group of the biofunctional molecule The following (a), (b-1), (b-2), (c), (d), (e), (f), (g), (h) and (l):

Group (III): A functional group capable of forming a covalent bond upon a reaction with an aldehyde group or a carboxy group of the biofunctional molecule The following (g), (i), (j) and (k):

Group (IV): A functional group capable of forming a covalent bond upon a reaction with an alkynyl group of the biofunctional molecule The following (g), (i), (j), (k) and (n):

Group (V): A functional group capable of forming a covalent bond upon a reaction with an azide group of the biofunctional molecule The following (l) and (m):

Group (VI): A functional group capable of forming a covalent bond upon a reaction with a halogenated alkyl group, an alkylsulfonic acid ester or an arylsulfonic acid ester of the biofunctional molecule The following (g) and (i).

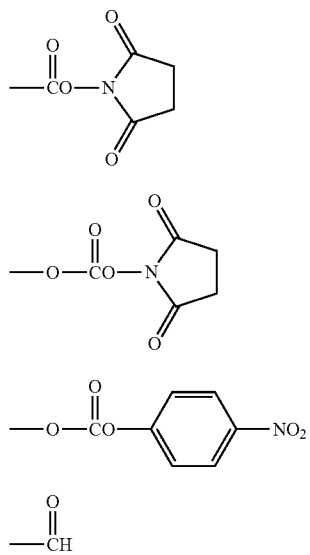

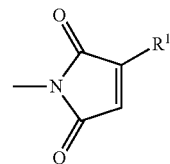

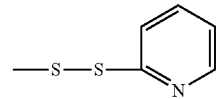

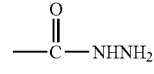

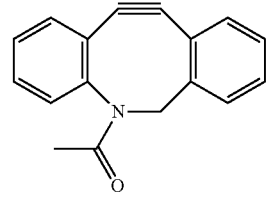

In the above formulae, $R^1$ and $R^3$ are each a hydrogen atom or a hydrocarbon group having from 1 to 5 carbon atoms, and example of the hydrocarbon group include an alkyl group, and specific hydrocarbon group includes a methyl group, an ethyl group, a propyl group, an isopropyl group, a butyl group, a tert-butyl group and a pentyl group. $R^2$ is a halogen atom selected from a chlorine atom, a bromine atom and an iodine atom.

$L^1$ in the formula (1) is a linker between glycerin and $X^1$, and is constituted with a covalent bond. Specifically, $L^1$ represents a single bond, —NH—, -$L^2$-$(CH_2)_{m1}$- or -$L^2$-$(CH_2)_{m1}$-$L^3$-$(CH_2)_{m2}$-, $L^2$ represents an ether bond, an amide bond, an urethane bond or a single bond, $L_3$ represents an ether bond, an amide bond or an urethane bond, and m1 and m2 represent each independently an integer of 1 to 5.

$L^1$ in the formula (1) is a linker between glycerin and a reactive functional group and is not particularly limited as far as it is a covalent bond, but $L^1$ is preferably a single bond, —NH—, an alkylene group, and an alkylene group containing at least one selected from a urethane bond, an amide bond, and an ether bond. As the alkylene group, preferably exemplified are a methylene group, an ethylene group, a trimethylene group, a propylene group, an isopropylene group, a tetramethylene group, a butylene group, an isobutylene group, a pentamethylene group, a hexamethylene group, and the like.

n in the formula (1) is an integer of 4 to 50, which represents the number of repeating units of ethylene oxide units, more preferably an integer of 6 to 48, and particularly preferably an integer of 8 to 24.

The intermediate of the branched monodispersed polyethylene glycol in the invention is represented by the formula (2):

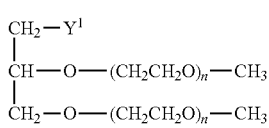

(2)

$Y^1$ in the formula (2) represents a hydroxyl group or an amino group. n is an integer of 4 to 50, which represents the number of repeating units of ethylene oxide units.

n in the formula (2) is an integer of 4 to 50, which represents the number of repeating units of ethylene oxide units, more preferably an integer of 6 to 48, and particularly preferably an integer of 8 to 24.

<Method for Producing Intermediate>

The intermediate of the invention can be obtained by the following production method. The method for producing the intermediate of the branched monodispersed polyethylene glycol comprises the step (A), the step (B) and the step (C).

[Step (A)]

The step (A) according to the invention is a step of subjecting a monodispersed polyethylene glycol derivative represented by the following formula (3):

and a compound represented by the following formula (4):

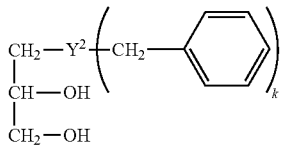

(4)

to a coupling reaction preferably in an anhydrous solvent in the presence of a strong base to obtain a compound represented by the following formula (5). Further, the compound represented by the above formula (3) added in excess is converted into a by-product represented by the following formula (6) in the step (A).

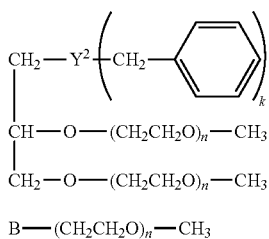

(5)

(6)

A in the formula (3) is a leaving group and is not particularly limited as far as it is a leaving group having a reactivity in the above coupling reaction, but examples thereof include a chloro group, a bromo group, an iodo group, a mesylate group, a tosylate group, a chloromethanesulfonate group and a trifluoromethanesulfonate group.

From the viewpoint of synthetic easiness, A is preferably a bromo group, a mesylate group, a tosylate group or a chloromethanesulfonate group, and more preferably a mesylate group.

n in the formula (3) is an integer of 4 to 50, which represents the number of repeating units of ethylene oxide units, more preferably an integer of 6 to 48, and particularly preferably an integer of 8 to 24.

$Y^2$ in the formula (4) is an oxygen atom or a nitrogen atom.

k in the formula (4) represents an integer of 1 or 2, and k is 1 when $Y^2$ is an oxygen atom and is 2 when $Y^2$ is a nitrogen atom.

The compound in which $Y^2$ in the formula (4) is an oxygen is 3-benzyloxy-1,2-propane-diol.

The compound in which $Y^2$ in the formula (4) is a nitrogen atom can be synthesized from 3-amino-1,2-propanediol suitably according known methods.

$Y^2$ in the formula (5) is an oxygen atom or a nitrogen atom.

k in the formula (5) is an integer of 1 or 2, and k is 1 when $Y^2$ is an oxygen atom and is 2 when $Y^2$ is a nitrogen atom.

n in the formula (5) is an integer of 4 to 50, which represents the number of repeating units of ethylene oxide units, more preferably an integer of 6 to 48, and particularly preferably an integer of 8 to 24.

B in the formula (6) is a functional group derived from the base catalyst used. For example, when the base catalyst in the coupling reaction is potassium hydroxide or sodium hydroxide, B is a hydroxyl group, when the base catalyst in the coupling reaction is sodium methoxide, B is a methoxy group, and when the base catalyst in the coupling reaction is sodium ethoxide, B is an ethoxy group.

n in the formula (6) is an integer of 4 to 50, which represents the number of repeating units of ethylene oxide units, more preferably an integer of 6 to 48, and particularly preferably an integer of 8 to 24.

The base catalyst in the coupling reaction is not particularly limited as far as it is a base catalyst with which the reaction proceeds. From the viewpoint of react the excessively added compound represented by the formula (3) with the base catalyst to convert the compound into the by-product represented by the formula (6) after the coupling reaction and then removing it into an aqueous layer by the extraction purification in the step (B), the by-product represented by the formula (6) is preferably one having a high solubility in an aqueous solution, and examples of the base catalyst include potassium hydroxide, sodium hydroxide, sodium methoxide, sodium ethoxide, and the like. Moreover, the amount of the base catalyst to be used is not particularly limited as far as the reaction proceeds, but is usually from 2.0 to 20 times, preferably from 2.1 to 10 times, relative to the compound represented by the formula (4), in molar ratio. In the case where the amount of the base catalyst to be used is less than the lower limit, the reaction does not completely proceed and there is a tendency that the monodispersed polyethylene glycol chain is not introduced into the hydroxyl group of the compound represented by the formula (4) and the hydroxyl group remains. On the other hand, in the case where the amount exceeds the upper limit, a side reaction may proceed due to the excess base.

The coupling reaction can be performed in a solvent. The solvent is not particularly limited as far as it is a solvent which does not react with the compounds represented by the formulae (3) and (4), and examples of the solvent include aprotic polar solvents such as tetrahydrofuran, acetonitrile, DMF (dimethylformamide), dichloromethane and chloroform, and mixtures thereof The amount of the solvent to be used is usually from 1.0 to 100 times, preferably from 2 to 50 times, and most preferably from 3 to 30 times, relative to the compound represented by the formula (3), in mass ratio. In the case where the amount of the solvent exceeds the upper limit, there is a tendency that the progress of the coupling becomes slow.

The reaction temperature of the coupling reaction varies depending on the solvent to be used or the like but is usually from 0 to 100° C. In the case where the reaction temperature is lower than the lower limit, the progress of the coupling reaction may become slow. On the other hand, in the case where the reaction temperature exceeds the upper limit, a side reaction may proceed due to the excessive temperature. Moreover, the reaction time of the coupling reaction varies depending on the conditions such as the reaction temperature but is usually preferably from about 1 to 48 hours.

The amount of the compound represented by the formula (3) to be used in the coupling reaction is usually from 2.0 to 10 times, preferably 2 to 4 times, relative to the compound represented by the formula (4), in molar ratio. In the case where the amount of the compound represented by the formula (3) to be used is less than the lower limit, the reaction does not completely proceed and there is a tendency that the hydroxyl group remains without introducing the monodispersed polyethylene glycol chain into the hydroxyl group of the compound represented by the formula (4). On the other hand, in the case where the amount exceeds the upper limit, the excess compound represented by the formula (3) becomes a waste and thus the production cost increases.

[Step (B)]

The step (B) according to the invention is a step of subjecting the compound represented by the above formula (5) (typically, a reaction product containing the compound represented by the formula (5)) to extraction purification.

In the step (A), the compound represented by the formula (3) added in excess is converted into the by-product, the compound represented by the formula (6), by the reaction with a base catalyst, and remains in the compound represented by the formula (5), which is a reaction product.

The step (B) is a step of extraction purification in which the by-product represented by the formula (6) contained in the target compound represented by the formula (5) dissolved in an organic solvent is removed into water (water may be provided as an aqueous solution).

In the step (B), since the target compound represented by the formula (5) has a hydrophobic benzyl group, it is easily distributed in an organic solvent, and since the by-product represented by the formula (6) does not contain a hydrophobic portion, it is easily distributed in water or an aqueous solution. In this way, the step is a step of extraction purification characterized in that only the by-product represented by the formula (6) is selectively separated.

As the organic solvent used in the step (B), ethyl acetate, toluene, chloroform, dichloromethane and the like may be exemplified, and from the viewpoint of solubility of the target compound represented by the formula (5), toluene, chloroform, dichloromethane and mixtures thereof are preferred. The amount of the organic solvent to be used is usually 2 to 30 times, preferably 3 to 20 times, relative to the reaction product containing the compound represented by the formula (5) and the by-product represented by the formula (6), in mass ratio. In the case where the amount of the organic solvent to be used is less than the lower limit, the compound represented by the formula (5) may be dissolved in water or an aqueous solution. On the other hand, in the case where the amount exceeds the upper limit, the washing efficiency of the by-product represented by the formula (6) tends to decrease.

The water or aqueous solution used in the step (B) is not particularly limited as far as it can dissolve the by-product represented by the formula (6), and examples thereof include ion-exchanged water and an aqueous solution of sodium chloride, potassium chloride or ammonium chloride, the salt concentration being from 0 to 25%. The amount of the water or the aqueous solution to be used is usually 2 to 30 times, preferably 3 to 20 times, relative to the reaction product containing the compound represented by the formula (5) and the by-product represented by the formula (6) in mass ratio. In the case where the amount of the water or the aqueous solution used is less than the lower limit, the washing efficiency of the by-product represented by the formula (6) decreases. On the other hand, in the case where the amount exceeds the upper limit, the compound represented by the formula (5) may dissolve in the aqueous layer.

In the step (B), as the ratio of the organic solvent to the water or the aqueous solution, the value of the organic solvent/water or the aqueous solution is from 0.2 to 3.0 in mass ratio, and the value is preferably from 0.5 to 2.0.

The preferable range of the temperature in the step (B) depends on n. In the case where n is from 6 to 10, the temperature is preferably from 1 to 25° C., more preferably from 5 to 20° C. In the case where n is from 11 to 50, the temperature is preferably from 1 to 15° C., more preferably from 1 to 10° C. In the case where the temperature exceeds the upper limit, the by-product represented by the formula (6) dissolves in the organic layer and hence cannot be removed. The number of times of the extraction purification is not particularly limited, and it is preferable to carry out the purification plural times while checking the by-product represented by the formula (6) contained in the organic solvent by TLC (thin layer chromatography) or MS (mass spectrometry) measurement, for example.

[Step (C)]

The step (C) according to the present invention is a step of performing a treatment of cleaving the benzyl group contained in the compound represented by the formula (5) to obtain the intermediate of the branched monodispersed polyethylene glycol represented by the formula (2), and preferably a step of subjecting the compound represented by the formula (5) to a catalytic hydrogenation treatment to obtain the branched monodispersed polyethylene glycol represented by the formula (2).

As the catalyst for the catalytic hydrogenation treatment, palladium carbon and palladium hydroxide carbon may be exemplified. The equivalent of the catalyst is usually 0.01 to 1 time, preferably 0.05 to 0.2 times, relative to the compound represented by the formula (5), in weight ratio. The catalytic hydrogenation can be carried out in a solvent. Examples of the solvent include water, methanol, ethanol, tetrahydrofuran, ethyl acetate, DMF and mixtures thereof. The amount of the solvent to be used is usually 1 to 100 times, preferably 2 to 50 times, and most preferably 3 to 30 times, relative to the compound represented by the formula (5), in mass ratio. In the case where the amount of the solvent to be used exceeds the upper limit, the progress of the catalytic hydrogenation tends to be delayed. The reaction temperature of the catalytic hydrogenation varies depending on the solvent to be used and the like, but is usually 0 to 100° C. In the case where the reaction temperature is lower than the lower limit, the progress of the reaction may be delayed. On the other hand, in the case where the reaction temperature is higher than the upper limit, an excessive temperature may cause the progress of a side reaction. The reaction time for the hydrolysis varies depending on conditions such as the reaction temperature, but is usually preferably about from 1 to 48 hours.

<Method for Producing Branched Monodispersed Polyethylene Glycol>

The branched monodispersed polyethylene glycol of the invention can be obtained by the production method of the present invention. In particular, as the method for producing the branched monodispersed polyethylene glycol represented by the formula (1) by converting the functional group $Y^1$ of the formula (2) into $L^1$-$X^1$ using the intermediate of the branched monodispersed polyethylene glycol represented by the formula (2), a known synthesis method can be appropriately used and is represented as a step (D).

[Step (D)-1]

For example, as a method for introducing an active carbonate group, there may be exemplified a method of allowing disuccinimidyl carbonate to react with the hydroxyl group ($Y^1$) of the intermediate represented by the formula (2) in the presence of a base such as triethylamine.

[Step (D)-2]

For example, as a method for introducing an active ester group, there may be exemplified a method of allowing tert-butyl acrylate to react with the hydroxyl group ($Y^1$) of the intermediate represented by the formula (2) in the presence of a base such as potassium hydroxide, hydrolyzing the resultant in the presence of an acid catalyst such as hydrochloric acid to form a carboxy group, and subsequently allowing the resultant to react with N-hydroxysuccinimide in the presence of a condensing agent such as 1-(3-dimethylaminopropyl)-3-ethylcarbodiimide hydrochloride.

[Step (D)-3]

For example, as a method for introducing a maleimide group, there may be exemplified a method of allowing 3-maleimidopropionic acid, maleimidobutyric acid or the like to react with a condensing agent such as 1-(3-dimethylaminopropyl)-3-ethylcarbodiimide hydrochloride and subsequently allowing the resultant to react with the amino group ($Y^1$) of the intermediate represented by the formula (2) and a method of allowing N-succinimidyl 3-maleimidopropionate or N-succinimidyl maleimidobutyrate to react with the amino group ($Y^1$) of the intermediate represented by the formula (2) in the presence of a base such as triethylamine.

[Step (D)-4]

For example, as a method for introducing a bromoacetamide group, there may be exemplified a method of allowing N-succinimidyl bromoacetate or the like to react with the amino group ($Y^1$) of the intermediate represented by the formula (2) in the presence of a base such as triethylamine.

[Step (D)-5]

For example, as a method for introducing an azido group, there may be exemplified a method of allowing 5-azidopentanoic acid to react with a condensing agent such as 1-(3-dimethylaminopropyl)-3-ethylcarbodiimide hydrochloride and subsequently allowing the resultant to react with the amino group ($Y^1$) of the intermediate represented by the formula (2).

A specific structure of $L^1$ of the formula (1) in a preferred embodiment of the invention and a typical synthesis example of the branched monodispersed polyethylene glycol having the $X^1$ will be described below, but the invention is not limited thereto.

(a) Synthesis of Compound Having Active Carbonate Group

The hydroxyl group ($Y^1$) of the intermediate represented by the above formula (2) is allowed to react with N,N'-disuccinimidyl carbonate in a dichloromethane solvent in the presence of trimethylamine to obtain a compound represented by the following formula (7).

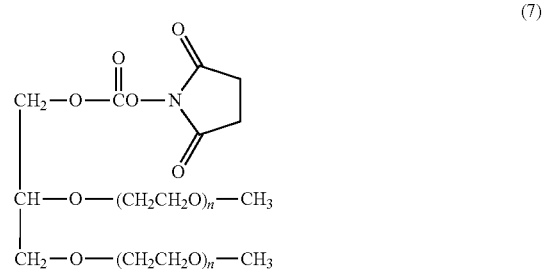

(b) Synthesis of Compound Having Active Ester Group

The hydroxyl group ($Y^1$) of the intermediate represented by the above formula (2) is allowed to react with tert-butyl acrylate in dichloromethane in the presence of potassium hydroxide, the resultant is hydrolyzed in the presence of hydrochloric acid to form a carboxy group, and subsequently allowing the resultant to react with N-hydroxysuccinimide in the presence of 1-(3-dimethylaminopropyl)-3-ethylcarbodiimide hydrochloride to obtain a compound represented by the following formula (8).

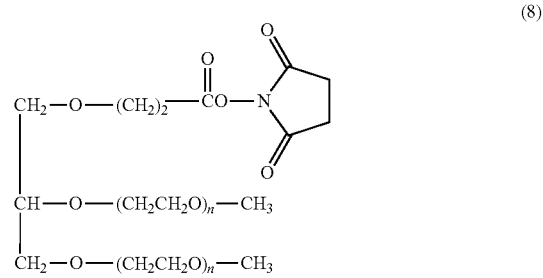

(c) Synthesis of Compound Having Maleimide Group

The amino group ($Y^1$) of the intermediate represented by the formula (2) is allowed to react with N-succinimidyl 3-maleimidopropionate in dichloromethane in the presence of trimethylamine to obtain a compound represented by the following formula (9).

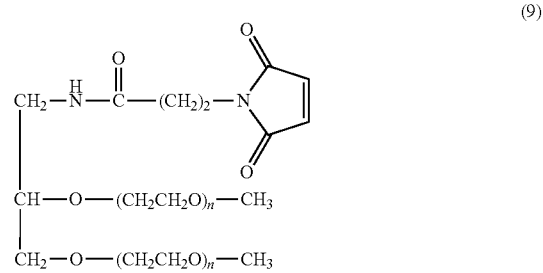

(d) Synthesis of Compound Having Bromoacetamide Group

The amino group ($Y^1$) of the intermediate represented by the formula (2) is allowed to react with N-succinimidyl bromoacetate in dichloromethane in the presence of trimethylamine to obtain a compound represented by the following formula (10).

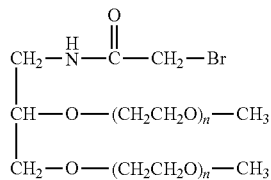

(10)

(e) Synthesis of Compound Having Azido Group

The amino group ($Y^1$) of the intermediate represented by the formula (2) is allowed to react with 5-azidopentanoic acid in dichloromethane in the presence of 1-(3-dimethylaminopropyl)-3-ethylcarbodiimide hydrochloride to obtain a compound represented by the following formula (11).

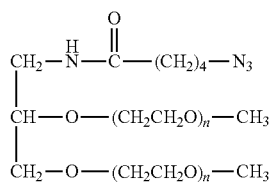

(11)

EXAMPLES

The present invention will be described more specifically with reference to Examples, but the invention should not be construed as being limited to the following Examples.

Example 1

Into a 500 mL four-necked flask equipped with a thermometer, a nitrogen inlet tube, a stirrer, a Dean-stark tube and a condenser tube were charged octaethylene glycol monomethyl ether (55.0 g, 143 mmol), toluene (275 g), triethylamine (18.8 g, 186 mmol) and methanesulfonyl chloride (18.0 g, 157 mmol), and the reaction was performed at 40° C. for 3 hours. Dichloromethane was added to dilute the mixture and then the resultant was washed with water, and the organic layer was dried over anhydrous magnesium sulfate. After filtration, the solvent was distilled off under reduced pressure to obtain a compound of the formula (12).

$^1$H-NMR (CDCl$_3$, internal standard TMS); δ (ppm):
3.08 (3H, s, —O—SO$_2$—C$\underline{H}_3$),
3.38 (3H, s, —O—C$\underline{H}_3$),
3.45-3.85 (30H, m, CH$_3$—O—(C$\underline{H}_2$C$\underline{H}_2$O)$_7$—C$\underline{H}_2$CH$_2$—O—SO$_2$—CH$_3$),
4.38 (2H, m, —C$\underline{H}_2$—O—SO$_2$—CH$_3$)

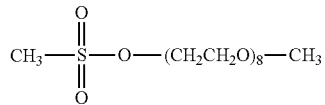

(12)

Example 2

Into a 500 mL four-necked flask equipped with a thermometer, a nitrogen inlet tube, a stirrer, a Dean-stark tube and a condenser tube were charged 3-benzyloxy-1,2-propanediol (3.43 g, 18.8 mmol), dehydrated THF (tetrahydrofuran) (67.5 g), the compound of the formula (12) (26.8 g, 48.9 mmol) and powdered potassium hydroxide (6.86 g, 122 mmol), and the reaction was performed at 50° C. for 8 hours. Powdered potassium hydroxide (0.951 g, 16.9 mmol) was added thereto and the mixture was stirred for a while. After the solvent was distilled off under reduced pressure, the mixture was diluted by adding dichloromethane (268 g). The organic layer was washed with a 25% aqueous ammonium chloride solution (268 g), a 25% aqueous sodium chloride solution (268 g) and ion-exchanged water (268 g) at 20° C. and then dried over anhydrous sodium sulfate. After filtration, the solvent was distilled off under reduced pressure to obtain a compound of the formula (13).

$^1$H-NMR (CDCl$_3$, internal standard TMS); δ (ppm):
3.38 (6H, s, —O—C$\underline{H}_3$),
3.40-3.80 (69H, m, —C$\underline{H}_2$—(OC$\underline{H}_2$C$\underline{H}_2$)$_8$—, —CH—(OC$\underline{H}_2$C$\underline{H}_2$)$_8$, —C$\underline{H}_2$O—CH$_2$Ph),
4.54 (2H, s, —CH$_2$O— C$\underline{H}_2$Ph),
7.27-7.38 (5H, m, arom. $\underline{H}$) (Ph means a phenyl group)

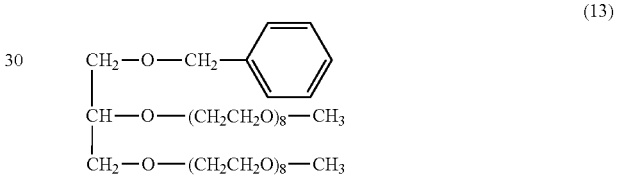

(13)

Example 3

Into a 500 mL four-necked flask equipped with a thermometer, a nitrogen inlet tube, a stirrer, a Dean-stark tube and a condenser tube were charged 5% palladium carbon (50% hydrous product) (11.1 g), the compound of the formula (13) (22.2 g, 24.3 mmol), methanol (702 g) and cyclohexene (34.0 g, 574 mmol), and the reaction was performed at 50° C. for 2 hours. After the palladium carbon was filtered off, the solvent was distilled off under reduced pressure, and the residue was dissolved in a 2.5% aqueous sodium chloride solution. After washing the aqueous layer with toluene, sodium chloride was dissolved so as to be a 20% aqueous sodium chloride solution, and extraction was performed using toluene. The organic layer was dried over anhydrous sodium sulfate, filtered, and then the solvent was evaporated under reduced pressure to obtain a compound of the formula (14).

$^1$H-NMR (CDCl$_3$, internal standard TMS); δ (ppm):
3.38 (6H, s, —O—C$\underline{H}_3$),
3.40-3.80 (69H, m, —C$\underline{H}_2$—(OC$\underline{H}_2$C$\underline{H}_2$)$_8$, —CH—(OC$\underline{H}_2$C$\underline{H}_2$)$_8$, —C$\underline{H}_2$OH),

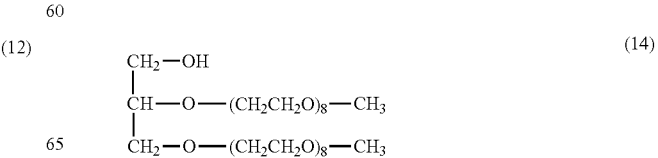

(14)

Example 4

Into a 100 mL three-necked flask equipped with a thermometer, a nitrogen inlet tube, a stirrer, a Dean-stark tube and a condenser tube were charged the compound of the formula (14) (3.53 g, 4.28 mmol), dichloromethane (101 g), 2,6-di-tert-butyl-p-cresol (0.7 mg) and N,N-disuccinimidyl carbonate (3.29 g, 12.8 mmol), and then triethylamine (1.38 g, 13.7 mmol) prepared in a dropping funnel was gradually added dropwise. After the dropwise addition was completed, the reaction was carried out at 25° C. for 6 hours. After washing with a 0.2 M citrate phosphate buffer solution (pH 2.5) to which sodium chloride was added so as to be a 15% aqueous sodium chloride solution, acetonitrile and hexane were added to the organic layer, and the resultant was washed with a 0.2 M citrate phosphate buffer solution (pH 7.0) and a 0.2 M citrate phosphate buffer (pH 3.0). The organic layer was dried over anhydrous sodium sulfate, filtered, and then the solvent was distilled off under reduced pressure to obtain a compound of the formula (15).

$^1$H-NMR (CDCl$_3$, internal standard TMS); δ (ppm):
2.84 (4H, s, -succinimide),
3.38 (6H, s, —O—C$\underline{H}_3$),
3.40-3.80 (67H, m, —C$\underline{H}_2$—(OC$\underline{H}_2$C$\underline{H}_2$)$_8$, —C$\underline{H}$—(OC$\underline{H}_2$C$\underline{H}_2$)$_8$),
4.35-4.50 (2H, m, —C$\underline{H}_2$—OCOO-succinimide)

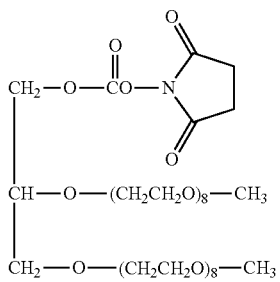

(15)

Example 5

Into a 500 mL four-necked flask equipped with a thermometer, a nitrogen inlet tube, a stirrer, a Dean-stark tube and a condenser tube were charged tetracosaethylene glycol monomethyl ether (55.0 g, 50.5 mmol), toluene (275 g), triethylamine (6.64 g, 65.6 mmol) and methanesulfonyl chloride (6.36 g, 55.5 mmol), and the reaction and purification were performed in the same manner as in Example 1 to obtain a compound of the formula (16).

$^1$H-NMR (CDCl$_3$, internal standard TMS); δ (ppm):
3.08 (3H, s, —O—SO$_2$—C$\underline{H}_3$),
3.38 (3H, s, —O—C$\underline{H}_3$),
3.45-3.85 (94H, m, CH$_3$—O—(C$\underline{H}_2$C$\underline{H}_2$O)$_{23}$—C$\underline{H}_2$C$\underline{H}_2$—O—SO$_2$—CH$_3$),
4.38 (2H, m, —C$\underline{H}_2$—O—SO$_2$—CH$_3$)

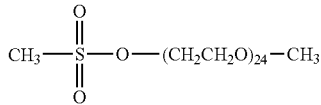

(16)

Example 6

Into a 500 mL four-necked flask equipped with a thermometer, a nitrogen inlet tube, a stirrer, a Dean-stark tube and a condenser tube were charged 3-benzyloxy-1,2-propanediol (3.43 g, 18.8 mmol), dehydrated THF (155 g), the compound of the formula (16) (61.3 g, 48.9 mmol) and powdered potassium hydroxide (6.86 g, 122 mmol), and the reaction was performed in the same manner as in Example 2. Powdered potassium hydroxide (0.951 g, 16.9 mmol) was added thereto and the mixture was stirred for a while. After the solvent was distilled off under reduced pressure, the mixture was diluted by adding dichloromethane (613 g). The organic layer was washed with a 25% aqueous ammonium chloride solution (613 g), a 25% aqueous sodium chloride solution (613 g) and ion-exchanged water (613 g) at 5° C. and then dried over anhydrous sodium sulfate. After filtration, the solvent was distilled off under reduced pressure to obtain a compound of the formula (17).

$^1$H-NMR (CDCl$_3$, internal standard TMS); δ (ppm):
3.38 (6H, s, —O—C$\underline{H}_3$),
3.40-3.80 (197H, m, —C$\underline{H}_2$—(OC$\underline{H}_2$C$\underline{H}_2$)$_{24}$—, —C$\underline{H}$—(OC$\underline{H}_2$C$\underline{H}_2$)$_{24}$, —C$\underline{H}_2$O—CH$_2$Ph),
4.54 (2H, s, —CH$_2$O—C$\underline{H}_2$Ph),
7.27-7.38 (5H, m, arom. $\underline{H}$) (Ph means a phenyl group)

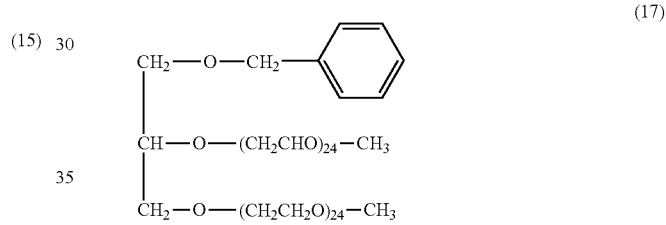

(17)

Example 7

Into a 500 mL four-necked flask equipped with a thermometer, a nitrogen inlet tube, a stirrer, a Dean-stark tube and a condenser tube were charged 5% palladium carbon (50% hydrous product) (11.1 g), the compound of the formula (17) (22.2 g, 9.55 mmol), methanol (702 g) and cyclohexene (18.5 g, 226 mmol), and the reaction and purification were performed in the same manner as in Example 3 to obtain a compound of the formula (18).

$^1$H-NMR (CDCl$_3$, internal standard TMS); δ (ppm):
3.38 (6H, s, —O—C$\underline{H}_3$),
3.40-3.80 (197H, m, —C$\underline{H}_2$—(OC$\underline{H}_2$C$\underline{H}_2$)$_{24}$, —C$\underline{H}$—(OC$\underline{H}_2$C$\underline{H}_2$)$_{24}$, —C$\underline{H}_2$OH),

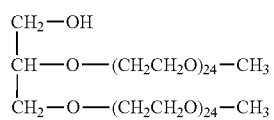

(18)

Example 8

Into a 100 mL three-necked flask equipped with a thermometer, a nitrogen inlet tube, a stirrer, a Dean-stark tube and a condenser tube were charged the compound of the formula (18) (3.53 g, 1.58 mmol), dichloromethane (39.8 g), 2,6-di-tert-butyl-p-cresol (0.7 mg), triethylamine (0.400 g, 3.95 mmol) and p-nitrophenyl chloroformate (0.637 g, 3.16 mmol), the reaction was carried out at 25° C. for 2 hours. After ion-exchanged water (171 mg, 9.48 mmol) was added thereto and the mixture was stirred for a while, hexane was added to the reaction mixture for dilution. After washing with a 25% aqueous sodium chloride solution, washing with a 0.2 M borate buffer (pH 10) and a 10% aqueous sodium chloride solution was further performed. The organic layer was dried over anhydrous sodium sulfate, filtered, and then the solvent was distilled off under reduced pressure to obtain a compound of the formula (19).

$^1$H-NMR (CDCl$_3$, internal standard TMS); δ (ppm):
3.38 (6H, s, —O—C$\underline{H}_3$),
3.40-3.80 (195H, m, —C$\underline{H}_2$—(OC$\underline{H}_2$C$\underline{H}_2$)$_{24}$, —C$\underline{H}$—(OC$\underline{H}_2$C$\underline{H}_2$)$_{24}$),
4.30-4.50 (2H, m, —C$\underline{H}_2$-OCOOPhNO$_2$),
7.37-8.33 (4H, m, -arom. $\underline{H}$) (Ph means a phenyl group)

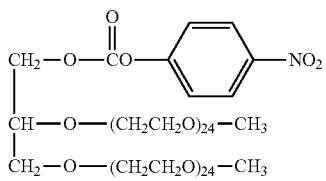

(19)

Example 9

Into a 500 mL four-necked flask equipped with a thermometer, a nitrogen inlet tube, a stirrer, a Dean-stark tube and a condenser tube were charged dodecaethylene glycol monomethyl ether (55.0 g, 98.1 mmol), toluene (275 g), triethylamine (12.9 g, 127 mmol) and methanesulfonyl chloride (12.4 g, 108 mmol), and the reaction and purification were performed in the same manner as in Example 1 to obtain a compound of the formula (20).

$^1$H-NMR (CDCl$_3$, internal standard TMS); δ (ppm):
3.08 (3H, s, —O—SO$_2$—C$\underline{H}_3$),
3.38 (3H, s, —O—C$\underline{H}_3$),
3.45-3.85 (46H, m, CH$_3$—O—(C$\underline{H}_2$C$\underline{H}_2$O)$_{11}$—C$\underline{H}_2$C$\underline{H}_2$—O—SO$_2$—CH$_3$),
4.38 (2H, m, —C$\underline{H}_2$—O—SO$_2$—CH$_3$)

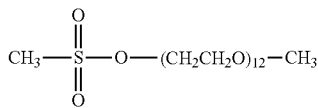

(20)

Example 10

Into a 500 mL four-necked flask equipped with a thermometer, a nitrogen inlet tube, a stirrer, a Dean-stark tube and a condenser tube were charged 3-benzyloxy-1,2-propanediol (3.43 g, 18.8 mmol), dehydrated THF (89.2 g), the compound of the formula (20) (35.4 g, 48.9 mmol) and powdered potassium hydroxide (6.86 g, 122 mmol), and the reaction was performed in the same manner as in Example 2. Powdered potassium hydroxide (0.951 g, 16.9 mmol) was added thereto and the mixture was stirred for a while. After the solvent was distilled off under reduced pressure, dichloromethane (354 g) was added to dilute the mixture. The organic layer was washed with a 25% aqueous ammonium chloride solution (354 g), a 25% aqueous sodium chloride solution (354 g) and ion-exchanged water (354 g) at 5° C. and then dried over anhydrous sodium sulfate. After filtration, the solvent was distilled off under reduced pressure to obtain a compound of the formula (21).

$^1$H-NMR (CDCl$_3$, internal standard TMS); δ (ppm):
3.38 (6H, s, —O—C$\underline{H}_3$),
3.40-3.80 (101H, m, —C$\underline{H}_2$—(OC$\underline{H}_2$C$\underline{H}_2$)$_{12}$—, —C$\underline{H}$—(OC$\underline{H}_2$C$\underline{H}_2$)$_{12}$, —C$\underline{H}_2$O—CH$_2$Ph),
4.54 (2$\underline{H}$, s, —CH$_2$O—C$\underline{H}_2$Ph),
7.27-7.38 (5H, m, arom. $\underline{H}$) (Ph means a phenyl group)

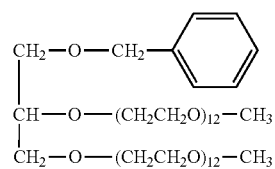

(21)

Example 11

Into a 500 mL four-necked flask equipped with a thermometer, a nitrogen inlet tube, a stirrer, a Dean-stark tube and a condenser tube were charged 5% palladium carbon (50% hydrous product) (11.1 g), the compound of the formula (21) (22.2 g, 17.5 mmol), methanol (702 g) and cyclohexene (34.0 g, 414 mmol), and the reaction and purification were performed in the same manner as in Example 3 to obtain a compound of the formula (22).

$^1$H-NMR (CDCl$_3$, internal standard TMS); δ (ppm):
3.38 (6H, s, —O—C$\underline{H}_3$),
3.40-3.80 (101H, m, —C$\underline{H}_2$—(OC$\underline{H}_2$C$\underline{H}_2$)$_{12}$, —C$\underline{H}$—(OC$\underline{H}_2$C$\underline{H}_2$)$_{12}$, —C$\underline{H}_2$OH),

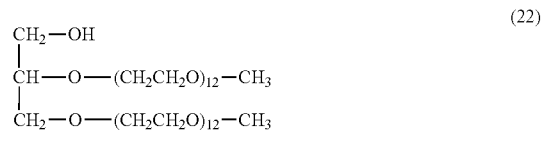

(22)

Example 12

Into a 100 mL three-necked flask equipped with a thermometer, a nitrogen inlet tube, a stirrer, a Dean-stark tube and a condenser tube were charged the compound of the formula (22) (10.6 g, 9.00 mmol), dichloromethane (70.5 g), phthalimide (1.85 g, 12.6 mmol) and triphenylphosphine (3.30 g, 12.6 mmol), and then diisopropyl azodicarboxylate (2.18 g, 10.8 mmol) prepared in a dropping funnel was gradually added dropwise thereto. After the dropwise addition was completed, the reaction was carried out at 25° C. for 1 hour. After adding methanol (0.346 g, 10.8 mmol) and stirring for a while, dichloromethane was distilled off under reduced pressure. The residue was dissolved in methanol (28.2 g), then ethylenediamine monohydrate (10.5 g, 135 mmol) was charged thereto, and the reaction was carried out at 40° C. for 1 hour. Toluene was added to the reaction mixture, and the mixture was washed with a 20% aqueous sodium chloride solution. After the organic layer was subjected to distillation under reduced pressure, the residue was dissolved in ion-exchanged water, the resultant was filtered, and then, while cooling to 10° C., the solution was adjusted to pH 6.0 with a 5% aqueous sodium dihydrogen phosphate solution and washed with ethyl acetate. Sodium chloride was added to the aqueous layer so as to be a 25% aqueous sodium chloride solution, and the mixture was extracted with chloroform. The organic layer was dried over anhydrous sodium sulfate and filtered, and then the solvent was distilled off under reduced pressure to obtain a compound of the formula (23).

$^1$H-NMR (CDCl$_3$, internal standard TMS); δ (ppm):
3.38 (6H, s, —O—C$\underline{H}_3$),
2.93-3.11 (2H, m, —C$\underline{H}_2$—NH$_2$),
3.40-3.80 (99H, m, —C$\underline{H}_2$—(OC$\underline{H}_2$C$\underline{H}_2$)$_{12}$, —C$\underline{H}$—(OC$\underline{H}_2$C$\underline{H}_2$)$_{12}$),

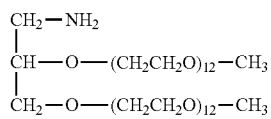

(23)

Example 13

Into a 100 mL three-necked flask equipped with a thermometer, a nitrogen inlet tube, a stirrer, a Dean-stark tube and a condenser tube were charged the compound of the formula (23) (3.53 g, 3.00 mmol), dichloromethane (177 g), 2,6-di-tert-butyl-p-cresol (1.06 mg) and N-succinimidyl 3-maleimidopropionate (0.958 g, 3.60 mmol), and then a dichloromethane solution of triethylamine (0.395 g, 3.90 mmol) prepared in a dropping funnel was gradually added dropwise. After the dropwise addition was completed, the reaction was carried out at 25° C. for 2 hours. After washing the reaction mixture with a 0.2 M citrate phosphate buffer solution (pH 2.5) to which sodium chloride was dissolved in a ratio of 15%, the organic layer was distilled off under reduced pressure. The residue was dissolved in a 0.2 M citrate phosphate buffer solution (pH 3.0) and, after the resulting solution was washed with adding toluene and dichloromethane, it was extracted with dichloromethane. The organic layer was washed with a 20% aqueous sodium chloride solution and then dried over anhydrous sodium sulfate. After filtration, the solvent was distilled off under reduced pressure to obtain a compound of the formula (24).

$^1$H-NMR (CDCl$_3$, internal standard TMS); δ (ppm):
2.51 (2H, t, —NHCO—C$\underline{H}_2$C$\underline{H}_2$—),
3.38 (6H, s, —O—C$\underline{H}_3$),
3.40-3.80 (99H, m, —C$\underline{H}_2$—(OC$\underline{H}_2$C$\underline{H}_2$)$_{12}$, —C$\underline{H}$—(OC$\underline{H}_2$C$\underline{H}_2$)$_{12}$, —C$\underline{H}_2$—NHCO—C$\underline{H}_2$C$\underline{H}_2$—),
6.69 (2H, s, -$\underline{maleimide}$),
6.86 (1H, t, —CH$_2$—N$\underline{H}$CO—)

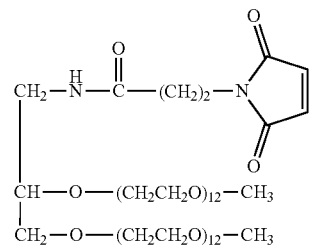

(24)

Example 14

Into a 100 mL three-necked flask equipped with a thermometer, a nitrogen inlet tube, a stirrer, a Dean-stark tube and a condenser tube were charged the compound of the formula (23) (2.35 g, 2.00 mmol), dichloromethane (120 g), 2,6-di-tert-butyl-p-cresol (0.7 mg) and N-succinimidyl bromoacetate (0.566 g, 2.40 mmol), and triethylamine (0.263 g, 2.60 mmol) prepared in a dropping funnel was gradually added dropwise thereto. After the dropwise addition was completed, the reaction was carried out at 25° C. for 1 hour. After adding acetic acid (0.312 g, 5.20 mmol) and stirring for a while, the reaction mixture was washed with a 20% aqueous sodium chloride solution adjusted to pH 2.0. The organic layer was dried over anhydrous magnesium sulfate, filtered, and then the solvent was distilled off under reduced pressure. The residue was again dissolved in a 20% aqueous sodium chloride solution adjusted to pH 2.0, and the aqueous layer was washed with toluene and then extracted with chloroform. The organic layer was dried over anhydrous magnesium sulfate, filtered, and then the solvent was distilled off under reduced pressure to obtain a compound of the formula (25).

$^1$H-NMR (CDCl$_3$, internal standard TMS); δ (ppm):
3.38 (6H, s, —O—C$\underline{H}_3$),
3.40-3.80 (99H, m, —C$\underline{H}_2$—(OC$\underline{H}_2$C$\underline{H}_2$)$_{12}$—, —C$\underline{H}$—(OC$\underline{H}_2$C$\underline{H}_2$)$_{12}$, —C$\underline{H}_2$—NHCO—),
4.10 (2H, s, —NHCO—C$\underline{H}_2$Br),
7.20 (2H, s, —N$\underline{H}$CO—),

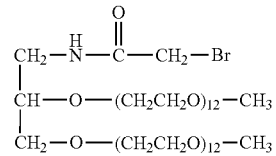

(25)

Example 15

Into a 100 mL three-necked flask equipped with a thermometer, a nitrogen inlet tube, a stirrer, a Dean-stark tube and a condenser tube were charged the compound of the formula (23) (2.35 g, 2.00 mmol), chloroform (14.0 g), Dibenzocyclooctyne-N-hydroxysuccinimidyl ester (0.877 g, 2.18 mmol) and 2,6-di-tert-butyl-p-cresol (0.5 mg), and then a chloroform solution (7.00 g) of triethylamine (0.239 g, 2.36 mmol) prepared in a dropping funnel was gradually added dropwise. After the dropwise addition was completed, the reaction was carried out at 25° C. for 4 hours. The reaction mixture was washed with 1M hydrochloric acid and a 25% aqueous sodium chloride solution, the organic layer was dried over anhydrous magnesium sulfate, filtered, and the solvent was distilled off under reduced pressure to obtain a compound of the formula (26).

$^1$H-NMR (CDCl$_3$, internal standard TMS); δ (ppm):
1.93-2.80 (4H, m, —C$\underline{H}_2$C$\underline{H}_2$—NCO—),
3.38 (6H, s, —O—C$\underline{H}_3$),
3.40-3.80 (102H, m, —C$\underline{H}_2$—(OC$\underline{H}_2$C$\underline{H}_2$)$_{12}$, —C$\underline{H}$—(OC$\underline{H}_2$C$\underline{H}_2$)$_{12}$, —C$\underline{H}_2$—NHCO—, —NCO—C$\underline{H}_2$—(1H)),
5.13 (1H, d, —NCO—C$\underline{H}_2$— (1H)),
6.84 (1H, s, —CH$_2$—N$\underline{H}$CO—),
7.25-7.45 (8H, m, -arom. H)

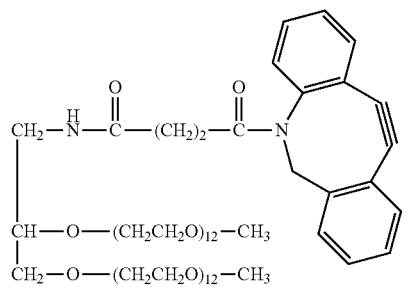

(26)

Example 16

Into a 100 mL three-necked flask equipped with a thermometer, a nitrogen inlet tube, a stirrer, a Dean-stark tube and a condenser tube were charged the compound of the formula (23) (2.35 g, 2.00 mmol), chloroform (17.5 g), 2,6-Di-tert-butyl-p-cresol (0.5 mg), 5-azidopentanoic acid (0.312 g, 2.18 mmol), 1-(3-dimethylaminopropyl)-3-ethylcarbodiimide hydrochloride (0.373 g, 2.40 mmol), and the reaction was carried out at 25° C. for 4 hours.

After the reaction mixture was filtered, the filtrate was washed with saturated aqueous sodium hydrogen carbonate and a 25% aqueous sodium chloride solution. The organic layer was dried over anhydrous magnesium sulfate, filtered, and then the solvent was distilled off under reduced pressure to obtain a compound of the formula (27).

$^1$H-NMR (CDCl$_3$, internal standard TMS); δ (ppm):
1.63-1.78 (4H, m, —NHCO—CH$_2$C$\underline{H}_2$C$\underline{H}_2$CH$_2$—N$_3$),
2.41 (2H, t, —NHCO—C$\underline{H}_2$—),
3.31 (2H, t, —C$\underline{H}_2$—N$_3$),
3.38 (6H, s, —O—C$\underline{H}_3$),
3.40-3.80 (101H, m, —C$\underline{H}_2$—(OC$\underline{H}_2$C$\underline{H}_2$)$_{12}$, —C$\underline{H}$—(OC$\underline{H}_2$C$\underline{H}_2$)$_{12}$, —C$\underline{H}_2$—NHCO—)

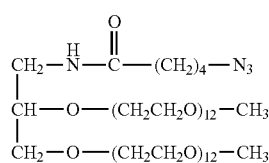

(27)

INDUSTRIAL APPLICABILITY

According to the present invention, there can be provided a highly pure branched monodispersed polyethylene glycol that effectively masks the hydrophobicity of a drug, an intermediate of the branched monodispersed polyethylene glycol, and production methods capable of easily obtaining the branched monodispersed polyethylene glycol and the intermediate.

While the present invention has been described in detail and with reference to specific embodiments thereof, it will be apparent to those skilled in the art that various changes and modifications can be made therein without departing from the spirit and scope of the invention.

The invention claimed is:

1. A branched monodispersed polyethylene glycol represented by formula (1) wherein 90% or more of PEG compounds constituting the branched monodispersed PEG have the same number of repeating ethylene oxide units n:

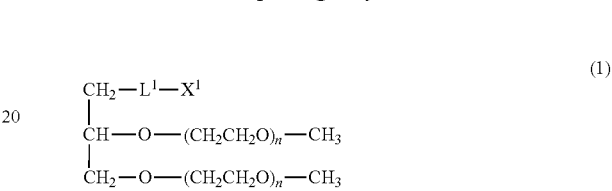

(1)

wherein, in the formula (1),
X$^1$ is a functional group that forms a covalent bond upon a reaction with a functional group present in a biofunctional molecule and is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group;
n is an integer of 8 to 24, which represents number of repeating units of ethylene oxide units; and
L$^1$ represents a single bond, —NH—, -L$^2$-(CH$_2$)$_{m1}$- or -L$^2$-(CH$_2$)$_{m1}$-L$^3$-(CH$_2$)$_{m2}$-, L$^2$ represents an ether bond, an amide bond, an urethane bond or a single bond, L$^3$ represents an ether bond, an amide bond or an urethane bond, and m1 and m2 represent each independently an integer of 1 to 5.

2. An intermediate of a branched monodispersed polyethylene glycol, which is represented by formula (2):

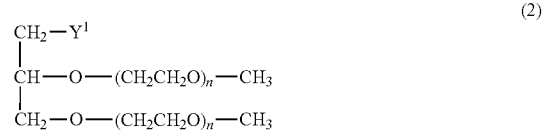

(2)

wherein, in the formula (2),
Y$^1$ is an amino group; and
n is an integer of 8 to 24, which represents number of repeating units of ethylene oxide units.

3. A method for producing the intermediate according to claim 2, wherein the following three steps:
a step (A) of coupling a monodispersed polyethylene glycol derivative represented by following formula (3) and a compound represented by following formula (4) to obtain a compound represented by following formula (5):

A-(CH$_2$CH$_2$O)$_n$-CH$_3$ (3)

wherein, in the formula (3),
A is a leaving group; and
n is an integer of 8 to 24, which represents number of repeating units of ethylene oxide units,

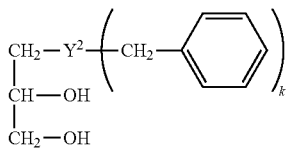
(4)

wherein, in the formula (4),
$Y^2$ is a nitrogen atom; and
k is an integer of 2,

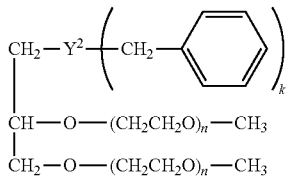
(5)

wherein, in the formula (5),
$Y^2$ is a nitrogen atom;
n is an integer of 8 to 24, which represents number of repeating units of ethylene oxide units, k is an integer of 2,
a step (B) of subjecting the compound represented by the formula (5) to extraction purification with water and an organic solvent, and
a step (C) of performing a treatment of cleaving the benzyl group contained in the compound represented by the formula (5) to obtain the intermediate of the branched monodispersed polyethylene glycol represented by the formula (2), are performed in the order of the step (A), the step (B) and the step (C).

4. The method according to claim 3, wherein the step (C) is effected by performing a catalytic hydrogen reduction treatment.

5. A method for producing the branched monodispersed polyethylene glycol according to claim 1, comprising a step (D) of converting $Y^1$ of an intermediate of a branched monodispersed polyethylene glycol, which is represented by formula (2) into $L^1$-$X^1$:

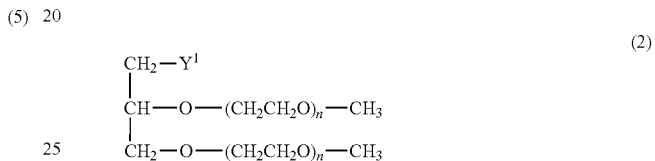
(2)

wherein, in the formula (2),
$Y^1$ is an amino group; and
n is an integer of 8 to 24, which represents number of repeating units of ethylene oxide.

* * * * *